United States Patent [19]

Schutt

[11] 4,248,861
[45] Feb. 3, 1981

[54] SKIN TREATMENT METHODS

[76] Inventor: Steven R. Schutt, 1080 Cambridge Rd., Teaneck, N.J. 07666

[21] Appl. No.: 13,467

[22] Filed: Feb. 21, 1979

Related U.S. Application Data

[60] Division of Ser. No. 861,304, Dec. 16, 1977, Pat. No. 4,154,823, which is a continuation of Ser. No. 694,769, Jun. 10, 1976, abandoned, which is a continuation-in-part of Ser. No. 533,534, Dec. 17, 1974, abandoned.

[51] Int. Cl.³ .............................................. A61K 7/44
[52] U.S. Cl. ...................................... 424/60; 424/232; 424/284; 424/195; 424/319; 424/DIG. 13
[58] Field of Search ................. 424/60, 195, DIG. 13, 424/319, 284, 232

[56] References Cited

U.S. PATENT DOCUMENTS

| 3,019,165 | 1/1962 | Mansor | 424/319 |
| 4,154,823 | 5/1979 | Schutt | 424/60 |

Primary Examiner—Dale R. Ore
Attorney, Agent, or Firm—Arthur Dresner

[57] ABSTRACT

A method for preventing deleterious effects of solar radiation by applying to human skin an effective amount of a composition or formulation comprising para-aminobenzoic acid, calcium-d-pantothenate, and a tocopherol compound, and desirably a gelling agent, is disclosed, along with methods of applying such compositions for use as a sunscreening agent, or for the treatment of skin ailments, particularly burns. To such compositions, a waxy extract of Kava may be included as a local anesthetic, along with a suitable carrier, such as a mixture of light unsaturated oils with stimulant agents.

4 Claims, No Drawings

SKIN TREATMENT METHODS

This application is a divisional application of Ser. No. 861,304 filed Dec. 16, 1977 now U.S. Pat. No. 4,154,823, presently copending and in allowable condition, which in turn was a continuation of application Ser. No. 694,769 filed June 10, 1976, now abandoned, which in turn was a continuation-in-part of application Ser. No. 533,534 filed Dec. 17, 1974, also now abandoned.

The present invention relates generally to skin treatment compositions or formulations and methods of using same, and more particularly to formulations or compositions useful for alleviating, minimizing or counteracting the harmful effects of excess exposure to or contact with, burn-inducing sources such as UV and infra-red radiation, sunlight, hot liquids such as water and oil, hot gases or vapors such as steam, electricity and the like.

A wide assortment of lotions, preparations or formulations have been proposed for local application as sun screens and suntan agents. Sun screen formulations are used to absorb or filter out the harmful rays of the sun which are in the range of 2950 Å to 3150 Å, while allowing solar rays of different wave lengths to pass through the skin in order to produce desirable tanning effects. Many such sun screen preparations have been useful for simply preventing burning effects of solar radiation by screening out the undesirable rays. These preparations usually contain basic UV radiation absorbers which are well known in the art.

Sun tan formulations differ from sun screen formulations in that their primary objective is to produce tanning effects, sunscreening being of secondary importance. A variety of sun tan devices have also heretofore been proposed for producing a tanning effect of the skin, such as by exposure to ultra violet radiation lamps which tend to excite natural pigmentation. Other methods to produce artificial tanning have been by using skin dyes such as erythrulose of various concentrations for various ranges of browning effects.

Few, if any of the prior types of formulations deal directly with the problem of injury to the skin cells which excessive exposure to burn-inducing sources can cause. For example, it is well known that excess exposure to sunlight enhances the aging process of human skin, causes blistering, dryness, tightening of skin surfaces and in some cases can even cause skin disease. Additionally, it is believed that excessive exposure to ultra violet radiation produces a loss of natural vitamin balance in the skin cell structure which results in the production of toxins and other undesirable and harmful effects. These undesirable effects tend to inhibit the healing process of sunburn or erythema. Most of the known sunscreening preparations which are useful in filtering out harmful radiation, however, have not been found to produce rapid restoration of normal skin conditions or to rapidly alleviate the deleterious effects of sunburning. The uses of para-amino benzoic acid (hereafter referred to as PABA) as a protective agent against solar sensitization or as a vitamin supplement are known (see "Lets Eat Right To Keep Fit," by Adelle Davis, published by The New American Library, Inc., Library of Congress Catalog Card No. 71-128463, pages 70, 71; and Merck Index, reference PABA); however experimentation has indicated that internal administration of PABA would require such massive dosages in order to be even minimally useful for alleviating the effects of over-exposure to solar radiation as to make treatment in this manner impractical.

Accordingly, it is an object of this invention to provide compositions or formulations which will not be subject to one or more of the above disadvantages.

Another object of this invention is the provision of such compositions useful for alleviating the harmful effects of excess exposure to, or contact with, burn-inducing sources.

Yet another object of this invention is the provision of such compositions which, in addition to possessing sun-screening properties, have the ability to and are therefore useful for rapidly restoring the vitamin balance to the structure of a skin cell in order to minimize the deleterious effects of sunburn and other burn-inducing sources.

Still another object of the present invention is to provide compositions for skin treatment which include an effective amount of certain vitamins for restoring the vitamin balance to the skin cell structure and to provide desirable therapeutic effects for alleviating the undesirable results of over-exposure to UV, infra-red and/or solar radiation and/or other burn-inducing sources.

A further object of the present invention is to provide formulations of the foregoing described type which will not break down over extended periods of time and will thus have desired long shelf life.

Yet a further object of the present invention is to provide a novel process for treating living animal skin to alleviate the harmful effects thereon of excessive exposure to, or contact with, burn-inducing sources.

Other objects and advantages will appear as the description proceeds.

The attainment of one or more of the above objects is made possible by my invention which includes a composition for treating living animal skin to alleviate the deleterious effects of burn-inducing sources thereon comprising, approximately to weight 5 to 20 parts of para-amino benzoic acid, 1 to 10 parts of calcium-d-pantothenate, and 0.5 to 1.5 parts of a tocopherol compound, in a cosmetically and therapeutically acceptable carrier.

Topical application of the above-described composition of this invention to living animal skin which has been subjected to a burn-inducing source, e.g. a 1st, 2nd or 3rd degree burn, results in a surprising reduction in healing time. When applied to sunburn-reddened areas of living animal skin, there results a surprisingly rapid (relative to untreated sunburned areas) elimination of the redness accompanied by a return of the normal vitamin balance in the skin cell structure, leaving the skin surface supple and substantially free of dryness or redness. When applied as a sunscreen agent prior to exposure, a surprising reduction or substantially complete prevention of reddening by the sunrays results.

The PABA and calcium-d-pantothenate components of these compositions are well known members of the vitamin B complex, and the tocopherol component is well known as providing vitamin E activity. While these materials, and various mixtures thereof, have been commonly administered internally to animals, their combination in the prescribed proportions in the topical compositions of this invention surprisingly enables the attainment of the desired burn healing and sunburn preventing results.

It is well known that tocopherol and its derivatives provide vitamin E activity, that the alpha form is much more active than the beta and gamma forms, that the "d" form (dextro) is more active than the "l" form (levo), that natural vitamin E occurs as the "d" form and synthetic vitamin E contains a mixture of both forms (dl), and that known tocopherol derivatives, e.g. mono and polycarboxylic acid esters including the acetate, succinate, propionate, oleate, etc., provide substantial and often advantageous vitamin E activity. Thus:

TABLE A

|  | Vitamin E International Units |
| --- | --- |
| 1 mg. dl-alpha tocopheryl acetate (synthetic) | = 1.0 I.U. |
| 1 mg. dl-alpha tocopherol (synthetic) | = 1.1 I.U. |
| 1 mg. d-alpha tocopheryl acetate (natural) | = 1.36 I.U. |
| 1 mg. d-alpha tocopheryl acid succinate (natural) | = 1.21 I.U. |
| 1 mg. d-alpha tocopherol (natural) | = 1.49 I.U. |

Accordingly, although any tocopherol compound may be employed, the alpha forms are preferred, particularly the d-alpha and dl-alpha forms, especially the free tocopherol alcohol form. In general the composition should contain a sufficient amount of the tocopherol compound, such as dl-alpha tocopherol, to assay out at about 150 to 500, preferably about 200 to 250, I.U. of vitamin E per fluid ounce.

As a highly preferred feature of the invention, it has been found that still further improved therapeutic effects are obtained by including in these compositions about 40 to 60 parts by weight of aloe, a well known substance in the form of inspissated juice of the leaves of the Aloe genus of plant, thickened as by evaporation. The Aloe vera species (Curacao Aloe) is preferred.

According to a further feature of the invention, the inclusion of a small amount such as about 0.5 to 3 parts by weight of Kava Kava in the instant compositions provides a highly desirable improvement and local anesthetizing effect. This well known substance, generally in the form of a waxy extract, is derived by extraction, as with acetone or ethyl ether or the like, of the decorticated and dried rhizome and roots of the plant Piper methysticum.

Yet a further feature of the invention resides in the inclusion in the instant composition of a small amount such as about 0.05 to 2 parts by weight of methyl salicylate to provide a highly desirable effect as a counterirritant and to assist in removing toxins from around the cell structures.

The compositions of this invention are applied in any well known cosmetically and therapeutically acceptable carrier or vehicle, preferably of oily type, employed in sufficient amount to yield readily spreadable compositions with the consistency of an emulsion, lotion, oil, slave, ointment or the like. Particularly preferred for this purpose are the normally liquid unsaturated vegetable oils, employed singly or in any desired mixtures thereof. Such oils, in which at least about 50% of the fatty acid components are mono- or polyunsaturated, are rapidly absorbed by the skin and thereby carry the essential vitamin components of the instant compositions into contact with burn-damaged cells or, when used for sunscreen purposes, prolong protective activity in that the absorbed or penetrated portions of the compositions resist removal from the skin surface by environmental and/or mechanical agencies. Generally about 25 to 50 parts of such oil or mixture thereof yields the desired consistency, those of lighter viscosity being preferred when a thinner, more rapidly penetrating composition is desired. As exemplary of such oils, there may be mentioned almond, apricot kernel, arachis, candlenut, castor, corn, cottonseed, croton, grapeseed, hazelnut, hempseed, olive, peach kernel, poppyseed, peanut, pumpkinseed, safflower, sesame, soybean, sunflower and walnut oils and the like.

The compositions of this invention may also contain small amounts of other known components of skin-treating compositions such as perfumes, thickeners, thinners, preservatives, antioxidants, surface active agents, coloring matter, organic solvents, water, stabilizers, demulcents, moisturizers, driers, stimulants, counterirritants, anesthetizers, antiseptics, antibiotics, antipruritics, lubricants, coagulants, steroids, UV absorbers, and the like. Illustratively, from about 1 to 10 parts by weight of a relatively saturated, higher melting, more viscous vegetable oil such as coconut oil may be included for thickening and/or bulking effects. These oils, and the above-described unsaturated vegetable oils also often have UV absorbing properties. Smaller amounts may be included, for example, of lanolin as a penetrant, lubricant and anti-drying agent, lemon oil as a fragrance and neutralizer, camphor for stimulation, absorption and removal of toxins from around the skin cells, Irish Moss as a thickener and demulcent, surfactants for solubilizing, emulsifying, dispersing, stabilizing and/or wetting functions, and water and organic solvents such as ethanol for solubilizing, thinning and the like.

The compositions of this invention are prepared in any desired manner and in any suitable order or sequence of addition of the various components and those skilled in the art will be readily cognizant of those available mixing procedures which are operative for the facile and expeditious production of such compositions. In use, the compositions are simply applied as a thin film or layer to the area of the skin which has been burned or which is to be protected from burning or reddening and left uncovered or covered as required or deemed advisable in any particular situation. These compositions may be dispensed in or from any suitable container in bulk or pressurized in aerosol form.

The following examples are only illustrative of preferred embodiments of my invention and are not to be regarded as limitative. All amounts and proportions referred to herein and in the appended claims are by weight unless otherwise indicated.

EXAMPLE 1

|  | Parts |
| --- | --- |
| PABA | 20 |
| Calcium-d-pantothenate | 10 |
| Alpha tocopheryl compound | 1.5 |
| Unsaturated Oil | 50 |

The alpha tocopheryl compound is d-alpha tocopherol, dl-alpha tocopherol or their acetate, propionate or acid succinate. The unsaturated oil is walnut, almond, safflower, soybean or peanut oil, or a mixture of 35% 1:1 walnut/almond oil, 20% safflower oil, 20% soybean oil and 25% peanut oil. This formulation provides improved and more rapid healing results when applied to 1st, 2nd or 3rd degree skin burns, and improved sunburn prevention when applied to the skin before exposure.

EXAMPLE 2

|  | Parts |
| --- | --- |
| PABA | 10 |
| Calcium-d-pantothenate | 5 |
| dl-alpha tocopherol | 1 |
| Aloe vera gel | 50 |
| Mixed unsaturated oils (as in Example 1) | 34 |

This formulation provides therapeutic results in addition to the somewhat similar results of the Example 1 formulation.

EXAMPLE 3

|  | Parts |
| --- | --- |
| PABA | 8 |
| Calcium-d-pantothenate | 4 |
| dl-alpha tocopherol | 1 |
| Kava-Kava (waxy extract) | 3 |
| Aloe vera gel | 50 |
| Mixed unsaturated oils (as in Example 1) | 34 |

This formulation provides local anesthetic properties in addition to the somewhat similar results obtained with the formulation of Example 2.

EXAMPLE 4

|  | Parts |
| --- | --- |
| PABA | 5 |
| Calcium-d-pantothenate | 1 |
| dl-alpha tocopherol | 1 |
| Kava-Kava (waxy extract) | 2 |
| Aloe vera gel | 55 |
| Methylsalicylate | 2 |
| Mixed unsaturated oils (as in Example 1) | 34 |

This formulation provides improved counterirritant and toxin removing results in addition to the somewhat similar results obtained with the formulation of Example 3.

EXAMPLE 5

|  | Parts |
| --- | --- |
| PABA | 7 |
| Calcium-d-pantothenate | 3 |
| dl-alpha tocopherol | 1 |
| Aloe vera gel | 43 |
| Mixed unsaturated oils (as in Example 1) | 34.8 |
| Coconut oil | 7 |
| Lanolin | 3 |
| Lemon Oil | 1 |
| Camphor | 0.2 |

The above formulation was used in a comparative test to determine its effectiveness. The subject was a 13 year old boy who had been over-exposed to solar radiation and had acquired second degree sunburn over approximately the same areas of the back of both of his legs. This formulation was applied to the entire affected areas of one leg and applied to only a portion of the affected areas on the other leg. The formulation was applied, approximately every forty-five minutes by hand, without rubbing, in an amount sufficient to cover the areas affected. After 5 to 6 applications the redness in the treated areas disappeared while it remained in the untreated areas. Additionally, the subject was relieved of the pain accompanying the burn in the treated areas.

EXAMPLE 6a

This example illustrates a particularly preferred embodiment.

|  | Parts |
| --- | --- |
| Part A |  |
| Mixed unsaturated oils (as in Example 1) | 30 |
| Coconut oil | 5.8 |
| Lanolin | 2.7 |
| Lemon | 0.7 |
| Camphor | 0.2 |
| dl-alpha tocopherol | 0.6 |
| (Part A to assay at about 500 I.U. vitamin E per fluid ounce.) |  |
| Part B |  |
| PABA | 6.6 |
| Calcium-d-pantothenate | 1.0 |
| Kava-Kava (waxy extract) | 1.0 |
| Methylsalicylate | 0.1 |
| Tween 80 (Reaction product of 1 mole sorbitan monooleate with 20 moles ethylene oxide, Atlas Powder) | 0.03 |
| Ethanol | 1.0 |
| Water | 0.27 |
| Part C |  |
| Aloe vera gel | 49.8 |
| Irish Moss | 0.2 |

Parts A and B are first blended together, and the resulting mixture thoroughly blended with Part C, the composition assaying at about 200 I.U. vitamin E per fluid ounce.

EXAMPLE 6b

The formulation of Example 6a was used to treat 40 cases of second degree sunburn. During the treatment, a portion of the affected area of each person's body was left completely untreated. A second portion of the affected area and in the same general vicinity as the first portion (such as on the same leg or the same arm) was treated with the Part A mixture of Example 6a and yet another portion also in the same general vicinity of the affected area was treated with the formulation of Example 6a. In all 40 cases after approximately six hours of application at 45 minute intervals dramatic results were observed in the areas treated with the formulation, in that the erythma or redness disappeared. There was no decrease of redness noticed in the other two areas. When a portion of the body was treated with oils containing *aloe vera* gel only slight decrease in redness was observed. Additionally, subjects treated with the formulation of Example 6a indicated that in those areas treated, significant pain relief was noticed as compared to the areas otherwise treated.

The following table illustrates the comparative results of the 40 cases on an average overall basis.

TABLE B

| Local Application of | Time Elapse | Effect on Erythma |
| --- | --- | --- |
| Aloe vera gel | 6 hours | Slight decrease in redness |
| Mixture of Part A, Example 6a | 6 hours | no effect |

TABLE B-continued

| Local Application of | Time Elapse | Effect on Erythma |
| --- | --- | --- |
| Formulation of Example 6a | 6 hours | redness disappeared |

EXAMPLE 6c

The formulation of Example 6a was applied to areas of the body in approximately 300 cases prior to exposure to solar radiation in varying amounts which might otherwise have produced erythma, but under varying conditions. In each case the formulation was applied by hand or with a gauze applicator in amounts sufficient to completely cover areas to be exposed to such radiation. No cases of erythma or sunburn equivalent to second degree burn was reported.

This invention has been disclosed with respect to certain preferred embodiments, and it will be understood that modifications and variations thereof obvious to those skilled in the art are to be included within the spirit and purview of this application and the scope of the appended claims.

I claim:

1. A method for preventing deleterious effects of solar radiation having wavelengths in the range of 2950 Å to 3150 Å on a human body comprising covering human skin with an effective amount of a composition comprising, approximately by weight, 5 to 20 parts of para-amino benzoic acid, 1 to 10 parts of calcium-d-pantothenate, and 0.5 to 1.5 parts of an alpha tocopherol compound, in a cosmetically acceptable carrier, said composition containing a sufficient amount of said alpha tocopherol compound to assay out at about 150 to 500 I.U. of vitamin E per fluid ounce.

2. A method for preventing deleterious effects of solar radiation having wavelengths in the range of 2950 Å to 3150 Å on a human body comprising covering human skin with an effective amount of a composition comprising, approximately by weight, 5 to 20 parts of para-amino benzoic acid, 1 to 10 parts of calcium-d-pantothenate, about 40 to 60 parts by weight of aloe, about 0.5 to 3 parts by weight of Kava Kava, about 0.05 to 2 parts by weight of methyl salicylate, and 0.5 to 1.5 parts of an alpha tocopherol compound in a cosmetically acceptable carrier, said composition containing a sufficient amount of said alpha tocopherol compound to assay out at about 150 to 500 I.U. of vitamin E per fluid ounce.

3. A method for preventing deleterious effects of solar radiation having wavelengths in the range of 2950 Å to 3150 Å on a human body comprising covering human skin with an effective amount of composition comprising, approximately by weight, 5 to 20 parts of para-amino benzoic acid, 1 to 10 parts of calcium-d-pantothenate, and 0.5 to 1.5 parts of an alpha tocopherol compound, in a cosmetically acceptable carrier comprising at least one normally liquid unsaturated vegetable oil, said composition containing a sufficient amount of said alpha tocopherol compound to assay out at about 150 to 500 I.U. of vitamin E per fluid ounce.

4. A method for preventing deleterious effects of solar radiation having wavelengths in the range of 2950 Å to 3150 Å on a human body comprising covering human skin with an effective amount of a composition comprising, approximately by weight, 5 to 20 parts of para-amino benzoic acid, 1 to 10 parts of calcium-d-pantothenate, and 0.5 to 1.5 parts of an alpha tocopherol compound which is dl-alpha tocopherol, in a cosmetically acceptable carrier comprising at least one normally liquid unsaturated vegetable oil, said composition containing a sufficient amount of said alpha tocopherol compound to assay out at about 150 to 500 I.U. of vitamin E per fluid ounce.

* * * * *